United States Patent
Bertus et al.

(10) Patent No.: US 10,562,868 B2
(45) Date of Patent: Feb. 18, 2020

(54) POLYFUNCTIONAL COMPOUNDS, METHODS FOR PREPARING SAME AND USES THEREOF

(71) Applicant: UNIVERSITE DU MANS, Le Mans (FR)

(72) Inventors: Philippe Bertus, Saint Saturnin (FR); Laurent Fontaine, Le Mans (FR); Morwenna Pearson-Long, Trange (FR); Fabien Boeda, Angers (FR); Julien Caille, Le Mans (FR); Valentin Gaignet, La Taillee (FR)

(73) Assignee: UNIVERSITE DU MANS, Le Mans (FR)

( * ) Notice: Subject to any disclaimer, the term of this patent is extended or adjusted under 35 U.S.C. 154(b) by 0 days.

(21) Appl. No.: 16/320,877

(22) PCT Filed: Jul. 4, 2017

(86) PCT No.: PCT/EP2017/066675
§ 371 (c)(1),
(2) Date: Jan. 25, 2019

(87) PCT Pub. No.: WO2018/019527
PCT Pub. Date: Feb. 1, 2018

(65) Prior Publication Data
US 2019/0161459 A1    May 30, 2019

(30) Foreign Application Priority Data

Jul. 27, 2016    (FR) ...................................... 16 57227

(51) Int. Cl.
*C07D 263/42*    (2006.01)
*G01N 33/532*    (2006.01)

(52) U.S. Cl.
CPC .......... *C07D 263/42* (2013.01); *G01N 33/532* (2013.01)

(58) Field of Classification Search
CPC .............................. C07D 263/42; G01N 33/532
USPC ........................................................ 548/228
See application file for complete search history.

(56) References Cited

U.S. PATENT DOCUMENTS 9,453,843 B2    9/2016    Fontaine et al.

FOREIGN PATENT DOCUMENTS

WO    2014/060357 A1    4/2014

OTHER PUBLICATIONS

International Search Report, dated Aug. 8, 2017, from corresponding PCT application No. PCT/EP2017/066675.
Beal et al., "Molecular Scaffolds Using Multiple Orthogonal Conjugations: Applications in Chemical Biology and Drug Discovery," Angew. Chem. Int. Ed. 2012, 51, pp. 6320-6326.
Boukattaya et al., "Simple and convenient access to α,α,α-trisubstitued amides by double addition of Grignard reagents to acyl cyanohydrins," Chem. Commun., 2012, 48, pp. 8655-8657.
Boukattaya et al., "A Short Access to Symmetrically α,α-Disubstituted α-Amino Acids from Acyl Cyanohydrins," Synthesis 2016, 48, pp. 906-916.
Casabona et al., "Simple and Efficient Multigram Scale Synthesis of 1-Aminocylopent-3-ene-1-carboxylic Acid," Synthesis 2006, No. 14, pp. 2440-2443.
Cotton et al. "Peptides containing dialkylglycines," Int. J. Peptide Protein Res. 28, 1986, pp. 230-244.
Genady et al., "Amphiphilic allylation of arylidene-1,3-oxazol-5(4H)-one using bis-π-allylpalladium complexes: an approach to synthesis of cyclohexyl and cylohexenyl α-amino acids," Org. Biomol. Chem., 2011, 9, 7180.
Ley et al., "Tetraproplyammonium Perruthenate, Pr4N+RuP4-, TPAP: A Catalytic Oxidant for Organic Synthesis," Synthesis, Jul. 1994.
Lindgren et al., "Preparation of Carboxylic Acids from Aldehydes (Including Hydroxylated Benzaldehydes) by Oxidation with Chlorite," Acta Chemica Scandinavica 27, 1973, pp. 888-890.
Lohmar et al., "alpha-Aminosauren als Nukleophile Acyläquivalente, IV. Synthese Symmetrischer Ketone unter Verwendung von 2-Phenyl-2-oxazolin-5-on", Chemische Berichte, vol. 113, 1980, pp. 3706-3715, XP002150545 (cited in ISR).
Neri et al., "Engineering of carbon based nanomaterials by ring-operating reactions of a reactive azlactone graphene platform," Chem. Commun., 2015, 51, 4846.
Sletten et al., "Bioorthogonal Chemistry: Fishing for Selectivity in a Sea of Functionality," Agnew. Chem. Int. Ed. 2009, 48, 6974-6998.
Valverde et al., "Click a la carte: robust semi-orthogonal alkyne protecting groups for multiple successive azide/alkyne cycloadditions," Tetrahedron 65 (2009) 7597-7602.
Hermanson, "Bioconjugate Techniques" Chapter 7: Trifunctional Crosslinkers, Elsevier, 2013, pp. 341-349.

*Primary Examiner* — Kristin A Vajda
(74) *Attorney, Agent, or Firm* — Young & Thompson (57) ABSTRACT

Disclosed are polyfunctional compounds of formula:

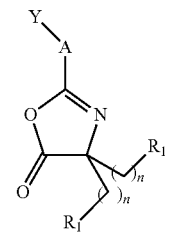

as well as methods for preparing same and the uses thereof, in particular in orthogonal or bioorthogonal processes.

22 Claims, 2 Drawing Sheets

POLYFUNCTIONAL COMPOUNDS, METHODS FOR PREPARING SAME AND USES THEREOF

The present invention relates to polyfunctional compounds, preparation methods and uses thereof, in particular uses thereof in orthogonal or bioorthogonal processes.

There is a strong demand for reactive compounds making it possible to produce (bio)orthogonal multiple chemical bonds. A chemical reaction is bioorthogonal if it does not interfere with biological processes. Click chemistry occupies an important place in this context (Beal and Jones, *Angew. Chem. Int. Ed.*, 2012, 51, 6320). A reaction will be considered as "click" if it meets the following criteria:
- high yield
- ease of implementation (aqueous environment)
- absence of by-product (or harmlessness of by-products formed).

The click chemistry reactions most often used in this field include the cycloadditions, for example the Huisgen 1,3-dipolar reaction or the Diels-Alder cycloaddition, the nucleophilic addition reactions by ring-opening and the hydrothiolation reactions (thiol-ene and thiol-yne).

While the hetero-bifunctional coupling reagents are very widespread, the hetero-polyfunctional compounds involving more than two distinct functionalities are rare in the prior art. Only 5 types of trifunctional compounds are described in the third edition of the work "*Bioconjugate Techniques*" by G. T. Hermanson (Elsevier, 2013, pp 341-349). Furthermore, in a certain number of cases the polyfunctional compounds currently available require protection/deprotection steps for their utilization (Valverde et al., *Tetrahedron*, 2009, 65, 7597).

International application WO2014060357 and the article by Neri et al., (*Chem. Commun.*, 2015, 51, 4846) describe compounds containing two orthogonal functions, i.e. addressable independently of each other: an azlactone ring on the one hand and a function capable of producing a Diels-Adler type 1,3-dipolar or [4+2] cycloaddition reaction on the other hand.

There is consequently a need to provide novel compounds comprising additional reactive functions that can be used in bioorthogonal processes to overcome the lack in the state of the art.

In the literature, two prior applications describe 4,4-diallyloxazolones (Cotton et al., *Int. J. Peptide Protein Res.*, 1986, 28, 230; Casabona and Cativiela, *Synthesis*, 2006, 2440). These compounds comprising an azlactone and two allyl functions are trifunctional. Their preparation is based on a nucleophilic substitution reaction in a basic medium (N,N-diisopropylethylamine or DIPEA) of the azlactones derived from N-acetylglycine and N-benzoylglycine in the presence of two equivalents of allyl iodide and allyl bromide respectively in dimethylformamide (DMF). After monoallylation, it has been described that certain of the 4-allyloxazolones undergo a sigmatropic rearrangement dependent on the nature of the group in position 2. This drawback thus limits the diallylation method to the N-benzoylglycine derivative.

Boukattaya et al. (*Chem. Commun.* 2012, 48, 8655-8657 and *Synthesis* 2016, 48, 906-916) describe a method for the preparation of N-acyl-α,α-diallylglycines involving the double addition of alkyl, alkenyl, aromatic or thiophenyl groups to the nitrile function of the acylcyanhydrines via the use of the organomagnesium compounds. This method offers direct access to the α,α-diallylglycines having both a carboxylic acid function and an acylated amine function.

However, the possibility of directly obtaining the diallyloxazolones by the cyclization of the α,α-diallylglycines has never been envisaged in the prior art.

There is therefore still a requirement to propose a simpler method making it possible to produce polyfunctional diallyloxazolones.

One of the aims of the present invention is to propose a family of novel reactive compounds comprising multiple functions capable of being involved in (bio)orthogonal processes and allowing a combination by means of covalent bonds between molecules of interest such as proteins, antibodies, peptides, DNA, RNA, siRNAs, miRNAs, biological markers, hormones, vitamins, lipids, monosaccharides, oligosaccharides, polysaccharides, glycans, synthetic chemical molecules, a natural or synthetic polymer.

The present invention also aims to propose a simple and effective method for preparing these novel compounds.

Another aim of the invention is to overcome the drawbacks of the state of the art by proposing novel coupling compounds:
- allowing combinations by means of bioorthogonal processes, both in vitro and in vivo,
- the reactive functionalities of which are also orthogonal with respect to each other,
- the high reactivity of which is compatible with biological media,
- allowing resistance to hydrolysis in aqueous medium,
- without forming any by-product that is toxic or difficult to eliminate,
- applicable to a wide range of biological or synthetic macromolecules,
- leading to robust chemical bonds and compatible with a very wide range of chemical functionalities as well as with biological media and living organisms, in vitro and in vivo.

The first subject of the present invention relates to a tetrafunctional compound of general formula (I), in which:
Y is a reactive functional group selected from the group comprising:
(i) a $N_3$, group
(ii) a ($C_2$-$C_{10}$) alkenyl group, optionally substituted with an aryl group or an arylalkyl group,
(iii) a ($C_2$-$C_{10}$) alkynyl group,
(iv) a ($C_3$-$C_{10}$) cycloalkenyl group, in particular a ($C_3$-$C_7$) cycloalkenyl group,
(v) a ($C_7$-$C_{10}$) cycloalkynyl group, more particularly a cyclooctynyl group or a cyclooctyne derivative,
(vi) an anthracenyl group, optionally substituted with a halogen or a linear or branched ($C_1$-$C_4$) alkyl,
(vi) a furanyl group, optionally substituted with a halogen or a linear or branched ($C_1$-$C_4$) alkyl,
(vi) a maleimidyl group, optionally substituted with a halogen or a linear or branched ($C_1$-$C_4$) alkyl, (vi) a tetrazinyl group, optionally substituted with a halogen or a linear or branched ($C_1$-$C_4$) alkyl,
(x) a group capable of a cycloaddition, A is a group selected from:
(a) a linear or branched —$(CH_2)_m$— alkylene chain, m being an integer from 0 to 20,
(b) an aromatic group of 6 to 14 carbon atoms, optionally substituted with at least one substituent selected from the group comprising the halogen atoms and the linear or branched ($C_1$-$C_4$) alkyl groups,
(c) a ($C_3$-$C_{18}$) cycloalkyl group, optionally substituted with at least one substituent selected from the group comprising the halogen atoms and the linear or branched ($C_1$-$C_4$) alkyl groups,
(d) a heterocyclic group comprising from 3 to 18 members, optionally substituted with at least one substituent selected from the group comprising the halogen atoms and the linear or branched ($C_1$-$C_4$) alkyl groups, $R_1$ is a ($C_2$-$C_{10}$) alkenyl group or a ($C_2$-$C_{10}$) alkynyl group n is an integer from 0 to 3.

By "alkyl" is meant a linear or branched saturated hydrocarbon-containing group. The term "($C_1$-$C_4$) alkyl" stands for a linear or branched saturated hydrocarbon-containing group having from 1 to 4 carbon atoms. By way of example, the methyl, ethyl, propyl, isopropyl, butyl, isobutyl, sec-butyl or tert-butyl groups may be mentioned.

Within the context of the present invention, the term "($C_1$-$C_6$) alkyl" stands for a linear or branched saturated hydrocarbon-containing group having from 1 to 6 carbon atoms. By way of example, the methyl, ethyl, propyl, isopropyl, butyl, isobutyl, sec-butyl or tert-butyl, pentyl and hexyl groups may be mentioned.

The term "($C_1$-$C_8$) alkyl" stands for a linear or branched saturated hydrocarbon-containing group having from 1 to 8 carbon atoms. By way of example, the methyl, ethyl, propyl, isopropyl, butyl, isobutyl, sec-butyl or tert-butyl, pentyl, hexyl, heptyl and octyl groups may be mentioned.

By the term "($C_2$-$C_{10}$) alkenyl group optionally substituted with an aryl group or an arylalkyl group" is meant, within the meaning of the present invention, any linear or branched hydrocarbon-containing group of 2 to 10 carbon atoms, optionally substituted with an aryl group or an arylalkyl group comprising one or more carbon-carbon double bonds.

By way of example, the vinyl, propenyl, allyl, butenyl, pentenyl, hexenyl, heptenyl, octenyl, nonenyl and decenyl groups may be mentioned.

Said alkenyl group can comprise a terminal double bond or a dienyl unit (conjugated double bond).

By the term "aryl" is meant the phenyl, naphthyl or biphenyl groups.

By the term "arylalkyl" is meant an aryl group substituted with an alkyl group.

The term "dienyl unit" stands for linear or cyclic hydrocarbon atoms having two double bonds separated by one single bond. By way of example, the butadienyl, isoprenyl, 2,3-dimethyl-1,3-butadienyl, 1,3-pentadienyl, 2-phenyl-1,3-butadienyl and furyl units may be mentioned.

By the term "($C_2$-$C_{10}$) alkynyl group" is meant, within the meaning of the present invention, any substituted or unsubstituted, linear or branched hydrocarbon-containing group of 2 to 10 carbon atoms, comprising one or more carbon-carbon triple bonds. Said alkynyl group can in particular comprise a terminal triple bond. The ethynyl, prop-1-ynyl, but-1-ynyl, but-2-ynyl, pentynyl, hexynyl, heptynyl, octynyl, nonynyl or decynyl group may be mentioned as examples of alkynyl groups.

By "($C_3$-$C_{10}$) cycloalkenyl group is meant a cyclic hydrocarbon-containing group of 3 to 10 carbon atoms comprising one or more carbon-carbon double bonds. The cyclopropenyl, cyclobutenyl, cyclopentenyl, cyclohexenyl, cycloheptenyl, cyclooctenyl, cyclononenyl or cyclodecenyl group may be mentioned as examples of the cycloalkenyl groups.

By "($C_7$-$C_{10}$) cycloalkenyl group is meant a cyclic hydrocarbon-containing group of 7 to 10 carbon atoms comprising one or more carbon-carbon triple bonds. The cycloheptynyl, cyclooctynyl, cyclononynyl and cyclodecynyl groups may be mentioned by way of example.

Such a cycloalkynyl group can be a cyclooctynyl group or derivatives thereof. Biarylazacyclooctynone (BARAC), dibenzocyclooctyne (DBCO), monofluorinated cyclooctynyl (MOFO), difluorinated cyclooctynyl (DIFO), ALO (aryl-less octyne), dimethoxyazacyclooctyne (DIMAC) and difluorobenzocyclooctyne (DIFBO) may be mentioned by way of examples of the cyclooctynyl group.

By "halogen" is meant: an iodine, bromine, chlorine or fluorine atom.

By the term "a group capable of participating in a cycloaddition" is meant, within the meaning of the present invention, any chemical group capable of implementing any type of cycloaddition known in the art, in particular a Diels-Alder cycloaddition, a Huisgen cycloaddition, a [3+2] cycloaddition, a "norbornene"-type cycloaddition, an "oxan-orbornadiene"-type cycloaddition, a "quadricyclane"-type ligation. The necessary chemical structures allowing the implementation of these reactions are known to a person skilled in the art. (M. B. Smith, J. March, *March*'s Advanced Organic Chemistry: Reactions, Mechanisms, and Structure, 6th Edition, Copyright John Wiley & Sons, Inc., 2007).

By "aromatic group of 6 to 14 carbon atoms" is meant a cyclic organic compound respecting Hückel's aromaticity rule, comprising from 6 to 14 carbon atoms. Said aromatic group can be a monocyclic or polycyclic aromatic group. The benzyl, phenyl, naphthyl, anthracenyl and tetracenyl groups may be mentioned by way of example.

The term "($C_3$-$C_{18}$) cycloalkyl group" denotes the alkyls the main carbon-containing chain of which is closed on itself forming a ring of from 3 to 18 carbon atoms. Cyclopropyl, cyclobutyl, ethylcyclobutyl, cyclopentyl, cyclohexyl, cycloheptyl, cyclooctyl, cyclononyl and cyclodecyl may be mentioned as examples.

The term "heterocyclic group comprising from 3 to 18 members" stands for any saturated or unsaturated heterocycle comprising from 3 to 18 members and containing from 1 to 3 heteroatoms selected from the group constituted by oxygen, nitrogen and sulphur. For example, the piperidinyl, pyrrolidinyl, piperazinyl, pyrazolyl, pyridyl, piridinyl, imidazolyl, furyl, morpholinyl, oxetanyl, tetrahydrofuranyl, tetra hydropyranyl, tetrahydrothienyl, thienyl and thiazolyl groups may be mentioned.

In a particular embodiment, the Y group represents a —CH=CH—$R_2$ group, $R_2$ representing:
either a hydrogen atom,
or a linear or branched ($C_1$-$C_8$) alkyl group,
or an aryl group, optionally substituted with a linear or branched ($C_1$-$C_8$) alkyl group.

In a more particular embodiment, the Y group is a vinyl (—CH=$CH_2$) group or an allyl (—$CH_2$—CH=$CH_2$) group.

In another particular embodiment, the Y group comprises a —CH═CH—CH═CHR$_4$ unit, R$_4$ being a hydrogen or a linear or branched C$_1$-C$_6$ alkyl group.

In a particular embodiment, the Y group represents a —C≡CR$_3$ group, R$_3$ representing:

either a hydrogen atom, or a linear or branched (C$_1$-C$_8$) alkyl group, or an aryl group, optionally substituted with a linear or branched (C$_1$-C$_8$) alkyl group, or a protective group of the alkyne function.

The protective groups of the alkyne function are well known to a person skilled in the art. The trialkylsilyls, in particular trimethylsilyl, triethylsilyl, tert-butyldimethylsilyl and benzyldimethylsilyl may be mentioned as examples. (P. G. M. Wuts, T. W. Greene, *Greene's Protective Groups in Organic Synthesis*, 4th Edn., John Wiley & Sons, Inc., 2007).

In a particular embodiment, the Y group is a (C$_3$-C$_7$) cycloalkenyl group, i.e. a cyclic hydrocarbon-containing group of 3 to 7 carbon atoms comprising one or more carbon-carbon double bonds. Cyclopropenyl, cyclobutenyl, cyclopentenyl, cyclohexenyl, cycloheptenyl, cyclohexa-1,3-dienyl, cyclohexa-1,4-dienyl or cyclopentadienyl may be mentioned by way of example.

In a particular embodiment, the A group is a phenyl, optionally substituted with at least one substituent selected from the halogens and the linear or branched (C$_1$-C$_4$) alkyl groups.

In another particular embodiment, the A group is a naphthyl group, optionally substituted with at least one substituent selected from the halogens and the linear or branched (C$_1$-C$_4$) alkyl groups.

The R$_1$ group of a compound of formula (I) of the invention is a (C$_2$-C$_{10}$) alkenyl group preferably comprising a terminal double bond or a (C$_2$-C$_{10}$) alkynyl group preferably comprising a terminal triple bond.

According to a particular embodiment of the invention, the compounds of formula (I) are those for which:

R$_1$ represents the —CH═CH$_2$ group;

n is equal to 1, said compound corresponding to general formula (Ia)

(Ia)

in which A and Y are as defined previously.

The present invention particularly relates to the compounds selected from the group comprising:

(Ia1)

(Ia2)

(Ia3)

(Ia4)

-continued

(Ia5)

(II)

in which Y and A are as defined above, and a compound of formula (IIIb)

(IIIb)

in which R₁ and n are as defined above, in order to obtain a compound of formula (IVb)

(Ia6)

(IVb)

in which Y, A, R₁ and n are as defined above;

(ii) oxidation of the compound of formula (IVb) in order to obtain a compound of formula (Vb)

(Vb)

According to another particular embodiment of the invention, the compounds of formula (I) are those for which:

R₁ represents the —C≡CH group;
n is equal to 1,
said compound corresponding to general formula (Ib)

in which Y, A, R₁ and n are as defined above;

(iii) cyclization of a compound of formula (Vb) in order to obtain a compound of formula (I).

The abovementioned method differs from the previous methods by two aspects: i) it offers the advantage of dispensing with an additional step of saponification of the ester function since the carboxylic acids are obtained directly and ii) it makes it possible, from the start of the synthesis, to introduce a variety of Y groups capable of being used in bioorthogonal processes, said groups being able to be introduced by N-acylation of the intermediate α,α-diallylaminoesters. In fact, the latter bear a very encumbered tertiary carbinamine function and only the N-acetylation reaction has been validated in the prior art.

This method offers effective access to polyfunctional 4,4-diallyl-oxazol-5(4H)-ones substituted in position 2 with an -A-Y group starting from acylcyanhydrines of formula (II) easily prepared with inexpensive reagents.

Step (ii) of said method can successively comprise step (iia) and step (iib).

Step (iia) consists of the oxidation of the compound of formula (IVb) in order to obtain a compound of formula (Vb')

(Ib)

in which A and Y are as defined previously.

A subject of the present invention is also a method for the preparation of the compounds of formula (I) of the invention as described above.

(Vb')

in which Y, A and n are as defined above.

Step (iib) consists of the oxidation of the compound of formula (Vb') in order to obtain a compound of formula (Vb).

The reaction conditions of steps (i), (iia) and (iib) of the above method are known to a person skilled in the art and described for example by Boukattaya et al. (*Synthesis* 2016, 48, 906-916).

Preferably, during the implementation of step (i) of the above method, a polar solvent such as tetrahydrofuran (THF) is used as solvent.

By way of example, step (iia), relating to the oxidation of alcohol to form aldehyde can be implemented by Ley's method, using the tetrapropylammonium perruthenate/N-Methylmorpholine-N-Oxide (TPAP/NMO) mixture as oxidant (Ley et al., *Synthesis*, 1994, 639-666).

Similarly, by way of example, step (iib), relating to the oxidation of aldehyde to form carboxylic acid, can be effected by Pinnick's oxidation (Lindgren et al., *Acta Chemica Scandinavica*, 1973, 27: 888.).

Step (iii) of the method as described above can be implemented by activation/dehydration for example using a chloroformate.

The present invention also relates to the intermediate compounds of formulae (IVb), (Vb') and (Vb), in which Y, A, $R_1$ and n are as defined previously.

Another subject of the present invention relates in particular to a novel method for preparing a compound of formula (Ia)

(Ia)

in which Y and A are as defined above, said method comprising the following steps:
(i) reaction between a compound of formula (II)

(II)

in which Y and A are as defined previously, and a compound of formula (IIIa)

(IIIa)

X being selected from F, Cl, Br and I,
in order to obtain a compound of formula (IVa)

(IVa)

in which Y and A are as defined above;
(ii) oxidation of the compound of formula (IVa) in order to obtain a compound of formula (Va)

(Va)

in which Y and A are as defined previously;
(iii) cyclization of a compound of formula (Va) in order to obtain the compound of formula (Ia).

Step (i) of this new method for the preparation of compounds of formula (Ia) consists of using organozinc compounds instead of organomagnesium compounds in order to obtain a compound of formula (IVa). This method offers a significant technical advantage over the use of the organomagnesium compounds such as, for example, allylmagnesium bromide, because no purification at the end of step (i) is necessary and the product is obtained quantitatively. The use of the organozinc compounds in step (i) allows the rapid and effective formation of α-disubstituted α-hydroxyamides.

Similarly to the method using organomagnesium compounds, the abovementioned method also makes it possible to effectively construct oxazolones having a wide range of substituents in position 2: alkenyls, alkynyles, cycloalkenyls, cycloalkynyles and aryls, etc.

Step (ii) of said method can successively comprise step (iia) and step (iib). Step (iia) consists of the oxidation of the compound of formula (IVa) in order to obtain a compound of formula (Va').

(Va')

in which Y and A are as defined previously; step (iib) consists of the oxidation of the compound of formula (Va') in order to obtain a compound of formula (Va).

The present invention also relates to the intermediate compounds of formulae (IVa), (Va') and (Va), in which Y and A are as defined previously.

The present invention provides heterotetrafunctional compounds, the different functionalities of which can be implemented selectively and independently of each other in order to lead to the ligation of two to four molecules of interest according to click chemistry reactions.

The first chemical function common to the compounds corresponding to formula (I) is of the azlactone type (5-(4H)-oxazolone). This group is known to react by ring opening with the primary amine functions in order to form a robust amide bond under mild conditions, in particular in aqueous solution. This reaction which does not require any catalyst, and does not form any by-product, is therefore compatible with biological media. The primary amine functions are very widespread in most biological molecules (proteins and nucleic acids in particular) and molecules of biological interest, which ensures a very wide field of application for the reagents of this invention.

The second and the third chemical functions of the compounds of formula (I) of the invention are bonded respectively to the two $R_1$ substituents which react with thiols by means of a thiol-ene or thiol-yne reaction.

In the context of the present invention the two $R_1$ groups present in a compound of formula (I) according to the present invention are identical and can react independently or successively with different molecules of interest.

The fourth chemical function of the compounds of formula (I) of the invention is the Y group which is a function capable of undergoing cycloaddition, polymerization, or hydrothiolation (thiol-ene or thiol-yne) reactions.

By a judicious combination of their different functions and the order in which they are subjected to the chemical conversions, these novel compounds make it possible to carry out bioorthogonal ligations by selective addressing of the different chemical functions present, with complete atom economy and without requiring steps of protection/deprotection.

The compounds of the present invention can be applied to a wide range of biological or synthetic (macro)molecules, whether proteins, nucleic acids, polysaccharides, markers (biological or synthetic) and biological polymers and molecules of interest generally. The chemical bonds formed between the molecules of interest and the compounds of the invention, such as triazole, gem-disubstituted amide and thioether, are robust and compatible with a very wide range of chemical functionalities as well as with biological media and living organisms, both in vitro and in vivo.

The four chemical functions present in the compounds according to the invention can react under different conditions, independently of each other. It is thus possible to trigger the reaction of one of these four groups without the other being converted, thus allowing successive chemoselective reactions.

The heterotetrafunctional compounds of formulae (I), (Ia), (Ia1), (Ia2), (Ia3), (Ia4), (Ia5), (Ia6) and (Ib) constitute novel ligation compounds for bioconjugation, diagnosis, therapy and the functionalization of surfaces.

The present invention also aims to propose a method for coupling between, at most, four different molecules of interest selected from the group comprising a biological molecule of interest, a natural or synthetic polymer, said molecules of interest being either molecules bearing a primary amine, or molecules bearing a sulphhydryl group, or molecules bearing a reactive function in order to implement a cycloaddition, a hydrothiolation, or a polymerization.

Said method comprises the following steps:
(i) bringing a compound of formula (I), (Ia) or (Ib) of the invention as described previously into contact with a first molecule of interest,
(ii) optionally, bringing said compound obtained at the end of step (i) into contact with a second molecule of interest,
(iii) optionally, bringing the compound obtained at the end of step (ii) into contact with a third molecule of interest,
(iv) optionally, bringing the compound obtained at the end of step (iii) into contact with a fourth molecule of interest.

A molecule of interest bearing a primary amine can react with the azlactone function of a compound of formula (I), (Ia) or (Ib) of the invention by azlactone ring opening.

A molecule of interest bearing a sulphhydryl group can react by hydrothiolation with an $R_1$ group of a compound of formula (I), (Ia) or (Ib) of the invention.

A molecule of interest bearing a reactive function for implementing a cycloaddition, a hydrothiolation, or a polymerization can react with the Y group of a compound of formula (I), (Ia) or (Ib) of the invention.

By "a reactive function for implementing a cycloaddition, a hydrothiolation, or a polymerization" is meant any function known in the prior art capable of participating in a cycloaddition, a hydrothiolation, or a polymerization. (M. B. Smith, J. March, *March's Advanced Organic Chemistry: Reactions, Mechanisms, and Structure*, 6th Edition, Copyright John Wiley & Sons, Inc., 2007).

The azide, alkynyl and cycloalkynyl groups and conjugated dienes may be mentioned by way of examples of functions capable of participating in a cycloaddition.

The alkenyl, cycloalkenyl and alkynyl groups may be mentioned by way of examples of functions capable of participating in a hydrothiolation.

An alkenyl group can also be involved in a polymerization.

According to the present invention, the biological molecules of interest are selected from the group comprising proteins, antibodies, peptides, DNA, RNA, siRNAs, miRNAs, biological markers, hormones, vitamins, lipids, monosaccharides, oligosaccharides, polysaccharides, glycans, synthetic chemical molecules such as anticancer or antiviral drugs or fluorescent or radioactive labels.

When a biological molecule of interest does not naturally comprise a primary amine, or a sulphhydryl group, or a reactive function for implementing a cycloaddition, a hydrothiolation or a polymerization, said molecule can previously undergo a functionalization reaction in order to integrate a primary amine, a sulphhydryl group or a reactive function in order to implement a cycloaddition, a hydrothiolation or a polymerization.

According to the present invention, a molecule of interest can also be a natural or synthetic polymer. For example, polypropylene or polyethylene having amine functions may be mentioned.

Said natural or synthetic polymer can form a reactive surface such as a film, a fabric, the contact surface of a microplate etc.

In a particular embodiment, the coupling method of the invention relates to a coupling between three different biological molecules of interest and a natural or synthetic polymer.

Said method can, for example, couple three biological molecules of interest with a polymer surface, such as that of a microplate.

In another particular embodiment, the coupling method of the invention relates to a coupling between four different biological molecules of interest.

According to the coupling method of the invention, it is possible to selectively introduce different molecules of interest onto the oxazolone structure of the compound of formula (I) of the invention by carrying out alkene hydrothiolation and nucleophilic addition reactions on the oxazolone or also cycloaddition reactions. Thus, the coupling method of the present invention can be used in methods such as for example:

grafting an antibody by hydrothiolation reaction,
introducing a fluorescent probe,
conjugation with a radiolabelled fragment,
introducing a chemical group inducing the formation of a water-soluble object (PEG etc.).

In a particular embodiment of the coupling method of the invention, the step relating to bringing a compound of formula (I), (Ia) or (Ib) into contact with a molecule of interest bearing a primary amine takes place before the step relating to bringing said compound into contact with another molecule of interest bearing a sulphhydryl function. This particular method makes it possible to introduce a molecule of interest bearing a sulphhydryl function onto a single $R_1$ function.

According to the present invention, said coupling process is a (bio)orthogonal method.

By "(bio)orthogonal method" is meant (E. M. Sletten, C. R. Bertozzi, Angew. Chem. Int. Ed. 2009, 48, 2-27) a method that can take place in a complex biological medium without denaturing it.

The reaction conditions for the cycloadditions, oxazolone opening or hydrothiolation are well known to a person skilled in the art.

The present invention also relates to a coupling kit comprising at least one compound of formula (I), (Ia), (Ia1), (Ia2), (Ia3), (Ia4), (Ia5), (Ia6) or (Ib) as described previously, as coupling reagent.

A subject of the present invention is also the use of at least one of the compounds of formula (I), (Ia), (Ia1), (Ia2), (Ia3), (Ia4), (Ia5), (Ia6) or (Ib) as described previously, as diagnostic reagent and an in vitro diagnostic method utilizing a compound of formula (I), (Ia), (Ia1), (Ia2), (Ia3), (Ia4), (Ia5), (Ia6) or (Ib) as described previously.

In fact, the coupling agents are useful in the field of diagnosis, in particular in the detection of reactions of the ligand-anti-ligand type such as antigen-antibody or protein-protein, because they make it possible to directly couple a biological molecule of interest, such as an antigen, to a so-called revelation molecule, such as an enzyme. The binding of the biological molecule of interest to another molecule, such as an antibody, is demonstrated by means of the revelation molecule. It may also be useful to couple a fluorescent probe to a biological molecule of interest for its detection by functional imaging.

The invention also aims to provide a composition comprising a compound of formula (I), (Ia) or (Ib) as described previously in combination with an aqueous or organic medium.

For example, dimethyl sulphoxide (DMSO), which is compatible with cell cultures, may be mentioned as organic medium.

The invention is illustrated in more detail below, by means of the examples and figures.

EXAMPLE 1

Protocol For The Preparation Of A Compound Of Formula (Ia).

Figure 1:
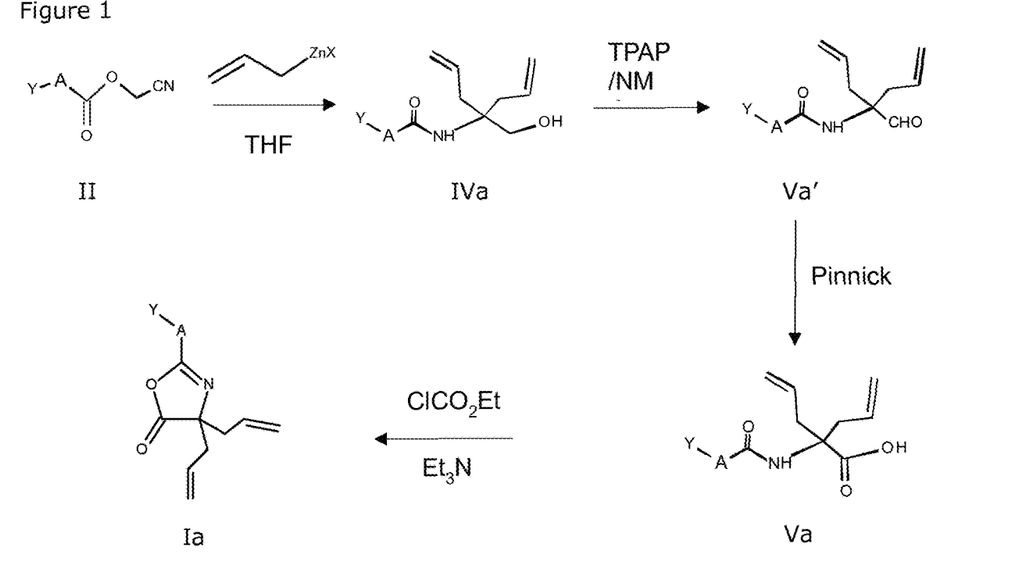
FIG. 1 shows the diagram of the method for the preparation of a compound of formula (Ia) of the invention.

This is illustrated in the diagram shown in FIG. 1.

1.1 Synthesis of the Compound of Formula IVa

Allyl bromide (3 mmol, 0.26 mL) is added dropwise to a two-necked flask provided with a refrigerant under argon, containing zinc (3.2 mmol, 209 mg) in suspension in 20 mL in THF and taken to reflux. The mixture is stirred at reflux for 90 minutes, then a solution of acylcyanhydrine of formula (II) (1 mmol) in 3 mL of THF is added dropwise. The mixture is stirred at reflux for 90 minutes, then is hydrolyzed by adding 10 mL of HCl (1M) at ambient temperature. The aqueous phase is extracted with ethyl acetate (2×20 mL). The organic phases are combined, basified with 2M NaOH, and washed with $NaCl_{sat}$. After drying over $MgSO_4$, filtration, and concentration under reduced pressure, the product of formula (IVa) is obtained pure.

1.2 Synthesis of the Compound of Formula (Va').

TPAP (0.05 mmol; 12 mg) and NMO (3 mmol, 351 mg) are added to a flask containing 4 Å molecular sieve (760 mg) and alcohol of formula (IVa) (1 mmol) obtained in step 1, in suspension in 10 mL in $CH_2Cl_2$. The mixture is stirred for 30 minutes under argon and filtered on silica gel, then the silica is washed with $CH_2Cl_2$. After concentration of the filtrate under reduced pressure, the aldehyde of formula (Va') is obtained pure.

1.3 Synthesis of the Compound of Formula (Va)

$NaH_2PO_4$, $2H_2O$ (0.5 mmol; 78 mg), $H_2O_2$ 38% (2 mmol; 0.2 mL) and 80% $NaClO_2$ (1.5 mmol; 170 mg) are added to a flask containing the aldehyde of formula (Va') (1 mmol) obtained in step 2, dissolved in 10 mL of acetonitrile cooled in an ice bath. The solution is stirred at ambient temperature for 2 hours, then $Na_2SO_3$ (0.8 mmol; 101 mg) is added. The reaction is left under stirring for 1 hour and 2 mL of aqueous solution of $KHSO_4$ (1M) is introduced. The aqueous phase is basified by adding a solution of NaOH (2M) then extracted with ethyl acetate (3×20 mL). The organic phases are combined, then washed with $NaHCO_3$sat (3×20 mL). The aqueous phases are combined, acidified with concentrated HCl to pH=3, then extracted with ethyl acetate (3×20 mL). After drying over $MgSO_4$, filtration, and concentration under reduced pressure, the acid of formula (Va) is obtained pure.

1.4 Synthesis of the Compound of Formula (Ia)

The acid of formula (Va) (1 mmol) is dissolved in triethylamine (1.5 mmol; 0.21 mL) and 5 mL of acetone in a flask, under an argon atmosphere. The mixture is cooled by means of an ice bath, then ethyl chloroformate (1 mmol; 0.1 mL) is added dropwise and the solution is stirred at 0° C. for 3 hours. The mixture is filtered on silica gel, then the silica is washed with Et$_2$O. After concentration of the filtrate under reduced pressure, the azlactone of formula (Ia) is obtained pure.

EXAMPLE 2

Synthesis of 4,4-Diallyl-2-(4-vinylphenyl)Oxazol-5 (4H)-one (Compound (Ia1))

The compound is synthesized according to the method described in example 1.

2.1/Synthesis of N-(4-(Hydroxymethyl)hepta-1,6-dien-4-yl)-4-vinylbenzamide

This compound, corresponding to the formula below, is obtained by the protocol of step 1.1 of example 1 in the form of an oil having a brown colour (Yield=quantitative).

NMR $^1$H (CDCl$_3$, 400 MHz): δ=7.67 (m, 2 H, Ar); 7.44 (m, 2 H, Ar); 6.73 (dd, 1 H, J=17.6 Hz, J=11.0 Hz, H$^2$); 6.41 (s, 1 H, NH); 5.9 (m, 2 H, H5, H'5); 5.83 (dd, 1 H, J=0.7 Hz, J=17.6 Hz, H1); 5.35(dd, 1 H, J=0.7 Hz, J=11.0 Hz, H1'), 5.22 (m, 4 H, H6, H6'); 3.76 (s, 2 H, H$^3$; 2.64 (m, 2 H, H4a, H4'a), 2.4 (m, 2 H, H4b, H4'b) ppm.

NMR $^{13}$C (CDCl$_3$, 100 MHz): δ=167.9; 141.1; 135.9; 133.7; 133.1; 127.3; 126.5; 119.9; 116.3; 67.9; 60.2; 38.9 ppm.

IR (film): ũ=3395, 2928, 1737. 1638, 1499, 914, 856, 780 cm$^{-1}$.

HRMS (ESI$^+$): m/z [M+Na]$^+$ calculated for C$_{17}$H$_{21}$NNaO$_2$: 294.1470; found: 294.1464.

2.2/Synthesis of N-(4-Formylhepta-1,6-dien-4-yl)-4-vinylbenzamide

This compound, corresponding to the formula below, is obtained by the protocol of step 1.2 of example 1 in the form of a brown-coloured solid (Yield=68%).

NMR $^1$H (CDCl$_3$, 400 MHz): δ=9.46 (s, 1 H, H3), 7.73 (m, 2 H, Ar); 7.44 (m, 2 H, Ar); 6.91 (s, 1 H, NH); 6.73 (dd, 1 H, J=17.6 Hz, J=10.7 Hz, H1); 5; 82 (d, 1 H, J=17.7 Hz, H$^2$); 5.66 (m, 2 H, H$^5$); 5.35 (d, 1 H, J=11; 0 Hz, H1'), 5.13 (m, 4 H, H6); 3.01 (dd, 2 H, J=14.3 Hz, J=7.3 Hz, H4a, H4'a); 2.66 (dd, 2 H, J=14.3 Hz, J=7.3 Hz, H4b, H4'b) ppm.

NMR $^{13}$C (CDCl$_3$, 100 MHz): δ=200.0; 166.6; 141.1; 135.9; 133.1; 131.5; 127.3; 126.5; 120.1; 116.6; 65.7; 37.0 ppm.

IR (film): ũ=3293, 2920, 2160, 1635, 1547, 1251, 925, 842, 763 cm$^{-1}$.

2.3/Synthesis of 2-allyl-2-(4-vinyl benzamido)pent-4-enoic Acid

This compound, corresponding to the formula below, is obtained by the protocol of step 1.3 of example 1 in the form of a white solid (Yield 58%).

RMN $^1$H (DMSO, 400 MHz): δ=12.6 (bs, 1H, COOH); 8.11 (s, 1 H, NH); 7.80 (m, 2 H, Ar); 7.57 (m, 2 H, Ar); 6.80 (m, 1 H, H2); 5.95 (dd, 1 H, J=17.7 Hz, J=0.8 Hz, H1); 5.71 (m, 2 H, H4); 5.37 (dd, 1 H, J=10.8 Hz, J=0.8 Hz, H1'); 5.08 (m, 4 H, H5); 2.75 (dd, 2 H, J=14.0 Hz, J=7.4 Hz, H3a, H3'a), 2.64 (dd, 1 H, J=14.0 Hz, J=7.4 Hz, H3b, H3'b) ppm.

NMR $^{13}$C (DMSO, 100 MHz): δ=173.4; 165.3; 139.9; 135.9; 133.5; 132.8; 127.6; 125.9; 118.6; 116.2; 61.4; 37.5 ppm.

IR (film): ũ=3365, 2924, 1713, 1600, 1525, 1333, 1220, 991, 916, 855 cm$^{-1}$.

HRMS (ESI$^+$): m/z [M+Na]$^+$ calculated for C$_{17}$H$_{20}$NO$_3$: 286.1443; found: 286.1429.

2.4/Synthesis of 4,4-Diallyl-2-(4-vinylphenyl)oxazol-5(4H)-one

The final compound (compound (Ia1)), corresponding to the formula below, is obtained by the protocol of step 1.4 of example 1 in the form of a clear yellow oil with a yield of 95%.

RMN $^1$H (CDCl$_3$, 400 MHz): δ=7.95 (m, 2H, Ar); 7.48 (3, 2H, Ar); 6.74 (dd, 1H, J=17.6 Hz, J=10.8 Hz, H2); 5.87 (d, 1H, J=17.6 Hz, H1); 5.66 (m, 2H, H4); 5.39 (d, 1H, J=17;

6 Hz, H1'); 5.13 (m, 4H, H5); 2.7 (dd, 2H, J=13.6 Hz, J=6.9 Hz, H3a, H3'a); 2.59 (dd, 2H, J=13.6 Hz, J=7.8 Hz, H3b, H3'b) ppm.

RMN $^{13}$C (CDCl$_3$, 100 MHz): δ=179.1; 159.9; 141.9; 135.9; 130.9; 128.3; 126.5; 124.9; 120.5; 116.7; 73.7; 41.1 ppm.

IR (film): ũ=3082, 2983, 1816, 1650, 1408, 1317, 1292, 1041, 972, 922, 890, 853, 709 cm$^{-1}$.

EXAMPLE 3

Synthesis of 4,4-Diallyl-2-(4-(Ethynyl)Phenyl)Oxazol-5(4H)-one (Compound (Ia2))

The compound is synthesized according to the method described in example 1.

3.1/Synthesis of N-(4-(Hydroxymethyl)hepta-1,6-dien-4-yl)-4-((trimethylsilyl)ethynyl)benzamide This compound, corresponding to the formula below, is obtained by the protocol of step 1.1 of example 1 in the form of a yellow-coloured solid (Yield=quantitative).

RMN $^1$H (CDCl$_3$, 400 MHz): δ=7.63 (m, 2 H, Ar); 7.51 (m, 2 H, Ar); 6.37 (s, 1 H, NH); 5.90 (m, 2 H, H2); 5.23 (m, 2 H, H4); 3.76 (s, 2 H, H4); 2.65 (dd, 2 H, J=13.8 Hz, J=6.5 Hz, H3a, H3'a); 2.38 (dd, 2 H, J=13.8 Hz, J=8.5 Hz, H3b, H3'b) 0.25 (m, 9 H, H5) ppm.

RMN $^{13}$C (CDCl$_3$, 100 MHz): δ=167.6; 134.3; 133.0; 132.3; 126.9; 126.8; 120.1; 104.0; 97.5; 68.1; 60.5; 39.1; 0.3 ppm.

HRMS (ESI$^+$): m/z [M+H]$^+$ calculated for C$_{20}$H$_{28}$NO$_2$Si: 342.1889; found: 342.889.

3.2/Synthesis of N-(4-Formylhepta-1,6-dien-4-yl)-4-((trimethylsilyl)ethynyl)benzamide This compound, corresponding to the formula below, is obtained by the protocol of step 1.2 of example 1 in the form of a brown oil (Yield 61%).

RMN $^1$H (CDCl$_3$, 400 MHz): δ=9.30 (s, 1 H, CHO); 7.73 (m, 2 H, Ar); 7.53 (m, 2 H, Ar); 5.64 (m, 2 H, H4); 5.14 (m, 4 H, H5); 3.07 (dd, 2 H, J=14.2 Hz, J=7.5 Hz, H3a, H3'a); 2.66 (dd, 2 H, J=14.2 Hz, J=7.5 Hz, H3b, H3'b') 0.3 (s, 9H, CH$_3$) ppm.

RMN $^{13}$C (CDCl$_3$, 100 MHz): δ=166.6; 133.2; 132.6; 131.2; 131.9; 128.0; 127.2; 120.5; 104.0; 66.3; 41.2; 35.9; 0.6 ppm.

HRMS (ESI$^+$): m/z [M+H]$^+$ calculated for C$_{20}$H$_{26}$NO$_2$: 340.1733; found: 340.1707.

IR (film): ũ=3293, 2158, 1741, 1629, 1525, 1251, 922, 842, 760 cm$^{-1}$.

3.3/Synthesis of 2-allyl-2-(4-ethynyl benzamido)pent-4-enoic Acid

This compound, corresponding to the formula below, is obtained by the protocol of step 1.3 of example 1 in the form of a yellow solid (Yield 50%).

RMN $^1$H (DMSO, 400 MHz): δ=12.6 (bs, 1 H, COOH); 8.23 (s, 1 H, NH); 7.82 (m, 2 H, Ar); 7.58 (m, 2 H, Ar); 5.71 (m, 2 H, H3); 5.07 (m, 4 H, H4); 4.37 (s, 1 H, H1); 2.74 (dd, 2 H, J=14.0 Hz, J=7.3 Hz, H3a, H3'a); 2.61 (dd, 2H, J=14.0 Hz, J=7.3 Hz, H3b, H3'b) ppm.

RMN $^{13}$C (DMSO, 100 MHz): δ=173.3; 165.0; 134.3; 132.7; 131.6; 124.9; 118.7; 82.8; 81.5; 61.4; 37.4 ppm.

3.4/Synthesis of 4,4-Diallyl-2-(4-(ethynyl)phenyl)oxazol-5(4H)-one (Compound (Ia2))

The final compound (compound (Ia2)), corresponding to the formula below, is obtained by the protocol of step 1.4 of example 1 in the form of a brown oil with a yield of 98%.

RMN $^1$H (CDCl$_3$, 400 MHz): δ=7.73 (m, 2H, Ar); 7.55 (m, 2H, Ar); 5.64 (m, 2H, H3); 5.13 (m, 4H, H4); 3.27 (dd,

2H, J=14.1 Hz, J=7.7 Hz, H2a, H2'a), 3.22 (s, 1H, H1); 2.70 (dd, 2H, J=14.1 Hz, J=7.0 Hz, H2b, H2'b) ppm.

NMR $^{13}$C (CDCl$_3$, 100 MHz): δ=176.6; 168.4; 133.7; 135.5; 131.5; 127.1; 126.3; 120.1; 82.6; 80.0; 66.0; 38.9 ppm.

IR (film): ũ=3283, 2980, 1721, 1609, 1531, 1499, 1235, 1097, 927, 855, 769 cm$^{-1}$.

EXAMPLE 4

Synthesis of 4,4-Diallyl-2-(Anthracen-9-yl)Oxazol-5(4H)-one (Compound (Ia3))

The compound is synthesized according to the method described in example 1.

4.1/Synthesis of N-(4-(Hydroxymethyl)hepta-1,6-dien-4-yl)anthracene-9-carboxamide This compound, corresponding to the formula below, is obtained by the protocol of step 1.1 of example 1 in the form of a yellow-coloured solid (Yield=96%).

RMN $^1$H (CDCl$_3$, 400 MHz): δ=8.47 (s, 1 H, Ar); 8.10 (dd, 2 H, Ar); 8.00 (dd, 2 H, Ar); 7.5 (m, 4 H, Ar); 6.23 (s, 1 H, NH); 5.9 (m, 2 H, H3, H3'); 5.15 (m, 4 H, H4, H4'); 5.97 (s, 2 H, H$^1$); 2.72 (dd, 2 H, J=13.7 Hz, J=6.9 Hz, H2a, H2'a); 2.50 (dd, 2 H, J=13.7 Hz, J=8.2 Hz, H2b, H2'b') ppm.

RMN $^{13}$C (CDCl$_3$, 100 MHz): δ=170.7; 132.3; 131.4; 131.1; 128.7; 128.6; 127.9; 127.0; 125.6; 124.8; 120.3; 67.8; 61.8; 39.5 ppm.

HRMS (ESI$^+$): m/z [M+H]$^+$ calculated for C$_{23}$H$_{24}$NO$_2$: 346.1807; found: 346.1798.

IR (film): ũ=2961. 2162, 1734, 1601, 1251, 1093, 842, 700 cm$^{-1}$.

4.2/Synthesis of N-(4-Formylhepta-1,6-dien-4-yl)anthracene-9-carboxamide

This compound, corresponding to the formula below, is obtained by the protocol of step 1.2 of example 1 in the form of a yellow solid (Yield 64%).

RMN $^1$H (CDCl$_3$, 400 MHz): δ=9.67 (s, 1 H, CHO); 8.45 (s, 1 H, Ar); 8.14 (m, 2 H, Ar); 7.98 (m, 2 H, Ar); 7.47 (m, 4 H, Ar); 6.66 (s, 1 H, NH); 5.77 (m, 2 H, H2); 5.22 (m, 4 H, H1); 3.1 (dd, 2 H, J=14.5 Hz, J=7.6 Hz, H3a, H3'a); 2.79 (dd, 2 H, J=14.6 Hz, J=7.0 Hz, H3b, H3'b) ppm.

RMN $^{13}$C (CDCl$_3$, 100 MHz): δ=199.5; 169.1; 131.2; 131.1; 130.7; 128.7; 128.6; 128.2; 126.8; 125.6; 124.8; 120.6; 66.0; 39.5 ppm.

HRMS (ESI$^+$): m/z [M+H]$^+$ calculated for C$_{23}$H$_{22}$NO$_2$: 344.1651; found: 344.1654.

IR (film): ũ=3200, 3034, 2922, 1737, 1616, 1525, 1439, 994, 924, 735 Cm$^{-1}$.

4.3/Synthesis of 2-allyl-2-(anthracene-9-carboxamido)pent-4-enoic Acid

This compound, corresponding to the formula below, is obtained by the protocol of step 1.3 of example 1 in the form of a yellow solid (Yield=35%).

RMN $^1$H (DMSO, 400 MHz): δ=13.0 (bs, 1H, COOH); 9.03 (s, 1 H, Ar); 8.24 (m, 2 H, Ar); 8.10 (m, 2 H, Ar); 7.56 (m, 4 H, Ar); 5.88 (m, 2 H, H2); 5.20 (m, 4 H, H1); 2.91 (dd, 2 H, J=14.4 Hz, J=7.0 Hz, H3a, H3'a); 2.60 (dd, 2 H, J=14.4 Hz, J=7.3 Hz, H3b, H3'b) ppm.

RMN $^{13}$C (DMSO, 100 MHz): δ=173.4; 167.8; 132.7; 132.5; 130.6; 128.2; 127.7; 127.2; 126.1; 125.5; 125.4; 119.0; 61.3; 37.7 ppm.

IR (film): ũ=3380, 2918, 1721, 1611, 1510, 1443, 1205, 1130, 909, 732 cm$^{-1}$.

HRMS (ESI$^+$): m/z [M+H]$^+$ calculated for C$_{23}$H$_{22}$NO$_3$: 360.1600; found: 360.1598.

4.4/Synthesis of 4,4-Diallyl-2-(anthracen-9-yl)oxazol-5(4H)-one (Compound (Ia3))

Compound (Ia3), corresponding to the formula below, is obtained by the protocol of step 1.4 of example 1 in the form of a yellow solid with a yield of 90%.

RMN ¹H (CDCl₃, 400 MHz): δ=8.61 (s, 1H, Ar); 8.30 (m, 2H, Ar); 8.05 (m, 2H, Ar); 7.52 (m, 4H, Ar); 5.96 (m, 2H, H2); 5.37 (m, 4H, H3); 2.86 (m, 4H, H1) ppm.

RMN ¹³C (CDCl₃, 100 MHz): δ=179.6; 160.3; 131.5; 131.2; 130.9; 130.4; 128.9; 127.5; 125.6; 125.2; 121.3; 121.1; 119.9; 41.5 ppm.

IR (film): ũ=2924, 2853, 1816, 1657, 1302, 1197, 1054, 994, 922, 734 cm⁻¹.

EXAMPLE 5

Coupling Process

Figure 2:
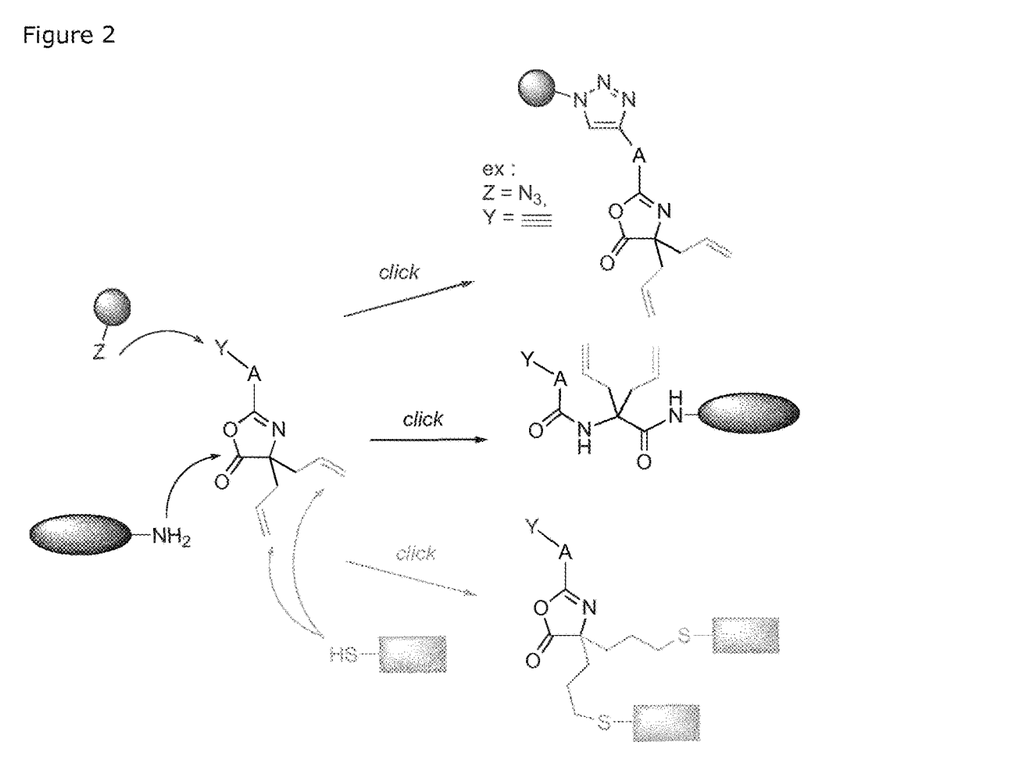
FIG. 2 shows different methods of coupling between a compound of the present invention and molecules of interest. The different types of molecules of interest are represented by round, oval or rectangular symbols. The function Z borne by a molecule of interest is a reactive function for implementing a cycloaddition, a hydrothiolation, or a polymerization.

Three types of coupling can be implemented by a compound of formula I of the present invention (FIG. 2).

5.1 Azlactone Ring Opening 0.1 mmol of a compound of formula (Ia2) with 0.6 mL of DMSO is introduced into a flask. Benzylamine is then introduced into the flask (11 μL, 0.1 mmol) and the mixture is heated at 40° C. for 24 hours. 3M HCl is added in a small quantity, then the mixture is extracted using diethyl ether (3×10 mL). The product corresponding to the formula below (N-(4-(benzylcarbamoyl)hepta-1,6-dien-4-yl)-4-ethynyl-benzamide) is recovered after passing through a rotary evaporator.

RMN ¹H (CDCl₃, 400 MHz): δ=7.68 (m, 2 H, Ar); 7.48 (m, 3 H, Ar); 7.29 (m, 4 H, Ar); 5.67 (m, 2 H, H4); 5.08 (m, 4 H, H5); 4.15 (s, 2 H, H1); 3.27 (dd, 2 H, J=13.7 Hz, J=7.7 Hz, H3a, H3'a); 3.19 (s, 1 H, H7); 2.65 (dd; 2 H; J=13.7 Hz; J=6.9 Hz; H3b; H3'b) ppm.

RMN ¹³C (CDCl₃, 100 MHz): δ=176.4; 165.7; 135.3; 132.9; 132.2; 129.3; 129.0; 128.7; 127.9; 126.9; 125.1; 118.8; 82.8; 79.4; 64.6; 44.1; 39.3 ppm.

IR: ν=3376; 3071; 2928; 2259; 1639; 1525; 1490; 1026 cm⁻¹

5.2 Cycloaddition Protocol

CuBr (0.32 mmol) is added to a Schlenk flask under argon containing 1 mmol of compound A obtained in the preceding step 5.1, 1 mmol of an azide B and pentamethyldiethylen-etriamine (PMDETA, 1.2 mmol) in suspension in 10 mL of degassed DMF. The mixture is left under stirring at ambient temperature for 24 hours. The reaction is illustrated below.

After the reaction, the mixture is diluted in 50 mL of dichloromethane (DCM) and washed with an aqueous solution of ethylenediaminetetraacatate (0.03 mol/L). After drying over MgSO$_4$, filtration, and concentration under reduced pressure, the product (N-(4-(benzylcarbamoyl)hepta-1,6-dien-4-yl)-4-(1-polyethyleneglycolmonomethylether-1H-1,2,3-triazol-4-yl)benzamide) is obtained in the form of a yellow solid.

Figure 3A:
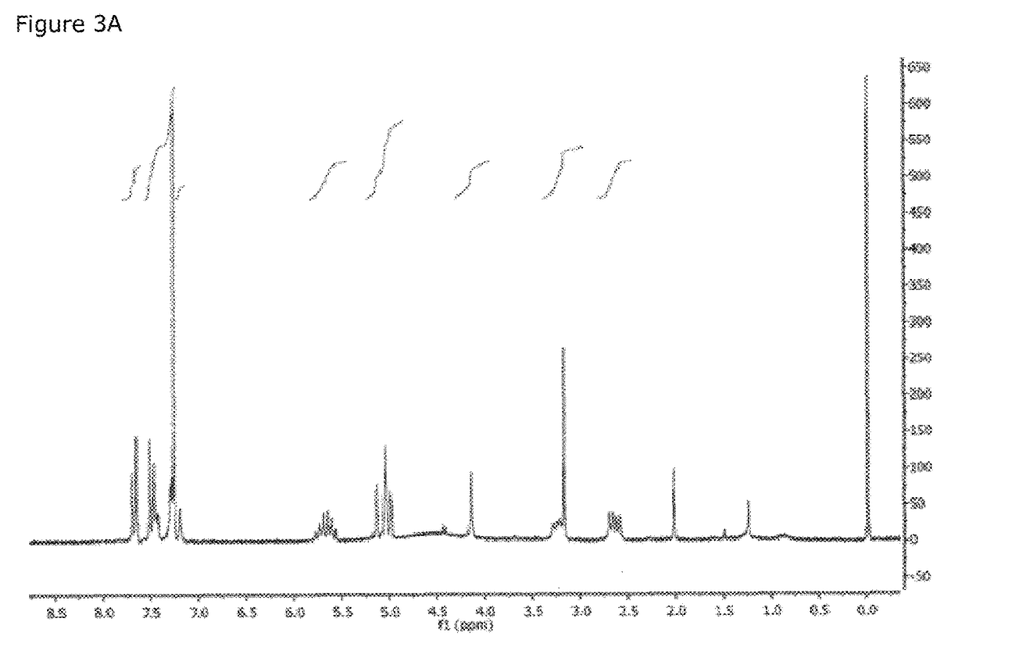
FIGS. 3A and 3B show the nuclear magnetic resonance (NMR) analysis (RMN) of the compound N-(4-(benzylcarbamoyl)hepta-1,6-dien-4-yl)-4-ethynylbenzamide (FIG. 3A) and of the compound N-(4-(benzylcarbamoyl)hepta-1,6-dien-4-yl)-4-(1-polyethyleneglycolmonomethylether-1H-1,2,3-triazol-4-yl)benzamide (FIG. 3B).
Figure 3B:
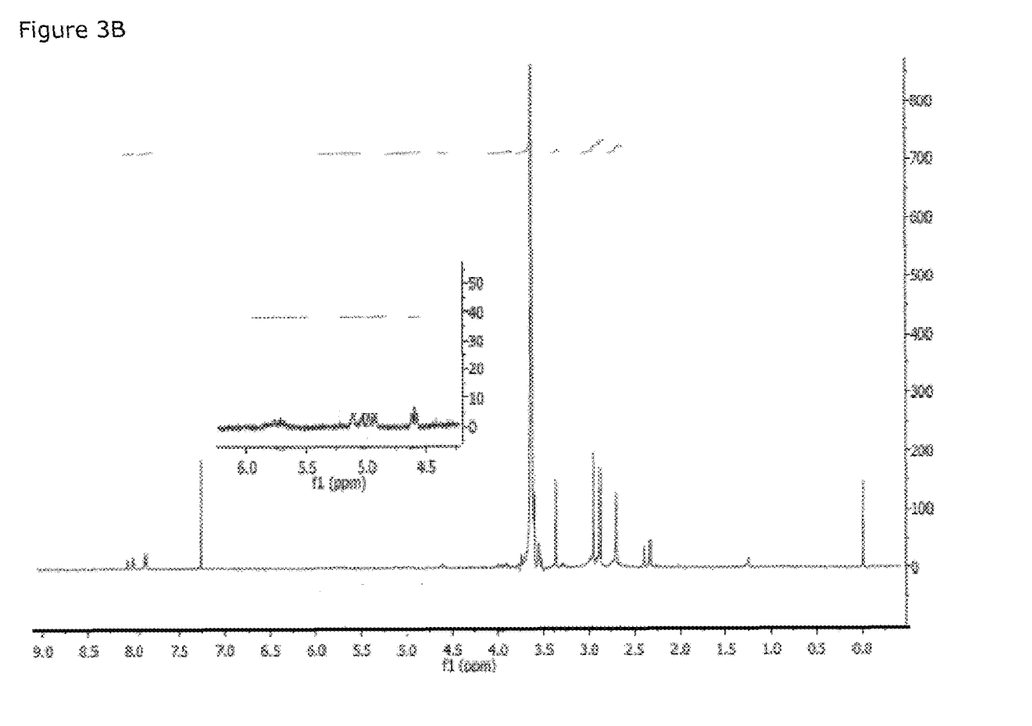

The cycloaddition product obtained is also characterized by proton nuclear magnetic resonance (FIGS. 3A and 3B) which shows that after reaction, the hydrogen peak of the alkyne corresponding to compound A (N-(4-(benzylcarbamoyl)hepta-1,6-dien-4-yl)-4-ethynylbenzamide) (FIG. 3A) has disappeared in favour of a new peak corresponding to the proton of the triazole ring of the cycloaddition product obtained (FIG. 3B).

The cycloaddition product obtained can also be analyzed by time-of-flight mass spectrometry (MALDI-TOF-MS) which shows a distribution of the signals separated by the mass of an ethylene oxide unit, i.e. 44 Da.

5.3 Hydrothiolation Protocol

Benzylmercaptan (2 mmol) and dimethoxyphenylacetophenone (0.1 mmol) are added to a flask under argon containing 1 mmol of a compound of formula I in suspension in 0.5 of dimethylformamide (DMF). The mixture is left under stirring at ambient temperature under UV for 1 hour, then concentrated under reduced pressure. Purification on silica gel is then carried out.

The invention claimed is:

1. Compound of general formula (I)

(I)

in which:
Y is a reactive functional group selected from the group consisting of:
(i) an N$_3$ group,
(ii) a (C$_2$-C$_{10}$) alkenyl group,
(iii) a (C$_2$-C$_{10}$) alkynyl group,
(iv) a (C$_3$-C$_{10}$) cycloalkenyl group,
(v) a (C$_7$-C$_{10}$) cycloalkynyl group,
(vi) an anthracenyl group,
(vii) a furanyl group,
(viii) a maleimidyl group, and
(ix) a tetrazinyl group,
A is a group selected from:
(a) a linear or branched —(CH$_2$)$_m$— alkylene chain, m being an integer from 0 to 20,
(b) an aromatic group of 6 to 14 carbon atoms,
(c) a (C$_3$-C$_{18}$) cycloalkyl group, and
(d) a heterocyclic group comprising from 3 to 18 members,
R$_1$ is a (C$_2$-C$_{10}$) alkenyl group or a (C$_2$-C$_{10}$) alkynyl group
n is an integer from 0 to 3.

2. Compound according to claim 1, in which
R$_1$ represents the —CH=CH$_2$ group;
n is equal to 1,
said compound corresponding to general formula (Ia)

(Ia)

in which A and Y are as defined in claim 1.

3. Compound according to claim 2, said compound being selected from the group consisting of:

(Ia1)

(Ia2)

(Ia3)

-continued (Ia4)

(Ia5)

(Ia6)

4. Compound according to claim 1, in which:
$R_1$ represents the —C≡CH group;
n is equal to 1,
said compound corresponding to general formula (Ib)

(Ib)

in which A and Y are as defined in claim 1.

5. Method for the preparation of a compound of formula (Ia) according to claim 1, comprising:

(i) reaction between a compound of formula (II)

(II)

in which Y and A are as defined in claim 1, and a compound of formula (IIIb)

(IIIb)

in which $R_1$ and n are as defined in claim 1,
in order to obtain a compound of formula (IVb)

(IVb)

in which Y, A, $R_1$ and n are as defined in claim 1;

(ii) oxidation of the compound of formula (IVb) in order to obtain a compound of formula (Vb)

(Vb)

in which Y, A, $R_1$ and n are as defined in claim 1;

(iii) cyclization of a compound of formula (Vb) in order to obtain a compound of formula (I).

6. Method for the preparation of a compound of formula (Ia)

(Ia)

in which Y and A are as defined in claim 1, said method comprising the following steps:

(i) reaction between a compound of formula (II)

in which Y and A are as defined in claim 1, and a compound of formula (IIIa)

X being selected from F, Cl, Br and I,
in order to obtain a compound of formula (IVa)

in which Y and A are as defined in claim 1;
(ii) oxidation of the compound of formula (IVa) in order to obtain a compound of formula (Va)

in which Y and A are as defined in claim 1;
(iii) cyclization of a compound of formula (Va) in order to obtain a compound of formula (Ia).

7. Method according to claim 6, wherein
step (ii) of said method successively comprises step (iia) and step (iib)
step (iia) consisting of the oxidation of the compound of formula (IVa) in order to obtain a compound of formula (Va′)

in which Y and A are as defined in claim 1;
step (iib) consisting of the oxidation of the compound of formula (Va′) in order to obtain a compound of formula (Va).

8. Method for coupling between, at most, four different molecules of interest selected from the group comprising a biological molecule of interest, a natural or synthetic polymer, said molecules of interest being either molecules bearing a primary amine, or molecules bearing a sulphhydryl group, or molecules bearing a reactive function in order to implement a cycloaddition or a polymerization, said method comprising the following steps:
(i) bringing a compound of formula (I), (Ia) or (Ib) according to claim 1 into contact with a first molecule of interest,
(ii) bringing said compound obtained at the end of step (i) into contact with a second molecule of interest,
(iii) bringing the compound obtained at the end of step (ii) into contact with a third molecule of interest,
(iv) bringing the compound obtained at the end of step (iii) into contact with a fourth molecule of interest.

9. Method according to claim 8, wherein the molecules of interest are selected from the group comprising proteins, antibodies, peptides, DNA, RNA, siRNAs, miRNAs, biological markers, hormones, vitamins, lipids, monosaccharides, oligosaccharides, polysaccharides, glycans and synthetic chemical molecules.

10. Method according to claim 8, wherein said method is a (bio)orthogonal method.

11. Coupling kit comprising at least one compound of formula (I), (Ia), or (Ib) according to claim 1, as coupling reagent.

12. Composition comprising a compound of formula (I), (Ia) or (Ib) according to claim 1 in combination with an aqueous or organic medium.

13. In vitro diagnostic method utilizing a compound of formula (I), (Ia) or (Ib) according to claim 1.

14. The compound of claim 1, wherein the ($C_2$-$C_{10}$) alkenyl group is substituted with an aryl group or an arylalkyl group.

15. The compound of claim 1, wherein the anthracenyl group, is substituted with a halogen or a linear or branched ($C_1$-$C_4$) alkyl.

16. The compound of claim 1, wherein the furanyl group is substituted with a halogen or a linear or branched ($C_1$-$C_4$) alkyl.

17. The compound of claim 1, wherein the maleimidyl group substituted with a halogen or a linear or branched ($C_1$-$C_4$) alkyl.

18. The compound of claim 1, wherein the tetrazinyl group substituted with a halogen or a linear or branched ($C_1$-$C_4$) alkyl.

19. The compound of claim 1, wherein the aromatic group of 6 to 14 carbon atoms is substituted with at least one substituent selected from the group comprising the halogen atoms and the linear or branched ($C_1$-$C_4$) alkyl groups.

20. The compound of claim 1, wherein the heterocyclic group comprising from 3 to 18 members is substituted with at least one substituent selected from the group comprising the halogen atoms and the linear or branched ($C_1$-$C_4$) alkyl groups.

21. The compound of claim 1, wherein the substituent Y is a ($C_3$-$C_7$) cycloalkenyl group.

22. The compound of claim 1, wherein the substituent Y is a cyclooctynyl group or a cyclooctyne derivative.

* * * * *